United States Patent [19]

Jochum et al.

[11] 4,351,853

[45] Sep. 28, 1982

[54] METHOD FOR PRODUCING PROSTHETIC DENTAL APPLIANCES BY PHOTOPOLYMERIZING A SHAPEABLE MASS

[75] Inventors: Peter Jochum, Hechendorf; Oswald Gasser, Seefeld, both of Fed. Rep. of Germany

[73] Assignee: Espe Fabrik Parmazeutischer Präparate G.m.b.H., Seefeld, Fed. Rep. of Germany

[21] Appl. No.: 302,412

[22] PCT Filed: Jan. 15, 1981

[86] PCT No.: PCT/DE81/00014

§ 371 Date: Sep. 11, 1981

§ 102(e) Date: Sep. 11, 1981

[87] PCT Pub. No.: WO81/01959

PCT Pub. Date: Jul. 23, 1981

[30] Foreign Application Priority Data

Jan. 17, 1980 [DE] Fed. Rep. of Germany ....... 3001616

[51] Int. Cl.$^3$ ............................................... C08F 2/46
[52] U.S. Cl. .................... 427/2; 204/159.23; 433/201; 433/202; 430/281; 427/54.1
[58] Field of Search ...................... 433/201, 202, 203; 204/159.23; 427/2; 433/199

[56] References Cited

U.S. PATENT DOCUMENTS

| | | | |
|---|---|---|---|
| 3,756,827 | 9/1973 | Chang | 96/86 P |
| 4,024,297 | 5/1977 | Gruber | 204/159.23 |
| 4,071,424 | 1/1978 | Dart et al. | 427/54 |
| 4,131,729 | 12/1978 | Schmitt | 204/159.23 |

FOREIGN PATENT DOCUMENTS

| | | |
|---|---|---|
| 1516456 | 4/1970 | Fed. Rep. of Germany . |
| 2419887 | 11/1974 | Fed. Rep. of Germany . |
| 1465897 | 3/1977 | United Kingdom . |

*Primary Examiner*—Sam Silverberg
*Attorney, Agent, or Firm*—Burns, Doane, Swecker & Mathis

[57] ABSTRACT

Prosthetic dental appliances of stable color and good mechanical properties can be produced by photopolymerization of one-component preparations which are stable during the storage, on the basis of ethylenically unsaturated monomers as well as fillers and dyes when using bicyclo-[2.2.1]-heptane-dione-2,3 compounds, if necessary together with amines, as photoinitiators for achieving sufficient penetration of the polymerization and whose inherent yellow color after short primary irradiation with visible light is bleached out for fixation permanently by intensive postirradiation with visible light.

9 Claims, No Drawings

METHOD FOR PRODUCING PROSTHETIC DENTAL APPLIANCES BY PHOTOPOLYMERIZING A SHAPEABLE MASS

For the production of the different prosthetic dental appliances, such as complete crowns, veneers of metal crowns as well as the visible part of dental bridge constructions, polymerizable masses on the basis of ethylenically unsaturated compounds are used on a large scale in addition to the ceramic materials. Due to their lower price, their easier processing and their lower brittleness, the appliances produced from plastic materials are frequently preferred to ceramic materials, especially since the ceramic appliances have an essentially higher hardness than the natural tooth substance, and thus, upon their use, the respective antagonist tooth is subjected to wear.

As monomer base for the production of the plastic materials and appliances, methylmethacrylate as well as difunctional or polyfunctional acrylic acid esters or methacrylic acid esters are mostly used as ethylenically unsaturated compounds, wherein fillers, dyes, fluorescent substances, and the like are added to the monomers prior to the polymerization for reduction of the shrinkage during the polymerization and for the increase of the mechanical strength as well as for the colour matching. to the natural teeth. Inter alia, previously pigmented beads of polymethacrylate or other pulverised organic polymerizates as well as also inorganic fillers, especially microfine fillers as e.g. pyrogenic silicic acid are suitable as fillers.

These monomer masses must be available in a wide range of shades for the production of esthetically unobjectionable appliances. Among them, there are also very light colours, e.g. for the masses used for the incisal part of the tooth and therefore, the raw materials must be feasible for the production of completely colourless polymerizates, thereby guaranteeing the colour stability up to more than one decade.

The polymerization and curing of the monomer preparations can be obtained in principle by the addition of conventional radical generating substances as polymerization catalysts. Due to the considerable demands on the colour stability, only the hot polymerization using peroxides, e.g. lauroylperoxide or benzoylperoxide has been proved useful. Due to the limited stability of the ready-prepared mixtures of monomer, fillers and additional ingredients as well as the peroxides, these masses are usually available as two component systems for the dental technician, wherein one of the components is a monomer preparation free of peroxide and the other a peroxide preparation free of monomer. Directly prior to the processing, both components are then mixed.

These two-component systems are, however, uncomfortable in the handling because of the required mixing step wherein incorrect dosage and, especially, an inhomogeneous mixture as well as inclusions of air within the mass lead to defects which jeopardize the success of the working. Moreover, the non-utilized residues of the respectively freshly prepared mixture must be discarded since they cannot be preserved.

Therefore, one-component systems have already been developed, having a photoinitiator system as radical generating substance. The curing of the polymerizable mass is then achieved by irradiation of light. Such preparations, which are stable during dark storage have been proved useful as tooth-filling materials in previous years. The photoinitiators such as benzoinalkylethers or benzilmonoketals, responding to UV-light, especially of a wave-length of 320 to 400 nm show, however, insufficient colour stability, especially in the very light dyeings required in crown materials and bridge materials, and lead, especially in the partly required darker dyeings of the monomer preparations to insufficient hardenings within the interior of the shaped bodies produced therefrom. Furthermore, the irradiation with UV-light requires technically complicated, and thus expensive, lamps which show a relatively poor durability, only.

The DE-OS No. 29 14 537 describes such mixtures for the production of tooth crowns, wherein benzil and benzoinalkylethers are used as photoinitiators. For achieving an improved curing, especially in the depth, peroxides are added in supplement to the polymerizable masses. This measure impairs, however, decisively the storing property of this preparation. Improved depths of curing can be achieved by 1,2-diketone compounds as photoinitiators responding to the short-wave portion of the visible light at wave-lengths of approximately 400 to 600 nm, especially when using together with amines as e.g. disclosed in the DE-OS No. 22 51 048. The usually clear inherent yellow colour of the 1,2-diketone initiators and the colour stability usually not meeting the requirements of prosthetic dental appliances produced therefrom, limites the application of these photosensitizers for the formulation of a one-component material suitable for the production of appliances like crowns and bridges.

Therefore, it is the object of the invention to provide a method for the production of crown and bridge constructions or the like appliances of plastic materials, which method meets all requirements, especially with regard to the colour stability and feasibility of dyeing of appliances and forecloses the disadvantages and possibilities of defects of the known two-component systems.

This object is solved thereby that within the monomer preparations, hardenable by irradiation, a bicyclo-[2.2.1]-heptane-dione-2,3 compound is used as photosensitizer preferably together with an amine as activator and that, after the polymerization, the light exposure is carried on until bleaching of the used photoinitiator is obtained. It was surprisingly recognized that the inherent yellow colour of these effective photoinitiators can be completely bleached by an intensive illumination subsequently added to the actual polymerization exposure so that unobjectionable shaped bodies of the polymerizate are then obtained with regard to colouring and colour stability. This specific "bleaching effect" of the initiators to be used according to the invention were not disclosed in the state of the art. Although, the DE-OS 22 51 048 also discloses a representative of the bicyclo-[2.2.1]-heptane-dione-2,3-compounds among the used 1,2-diketone compounds, namely the camphor quinone, the method, however, discloses no bleaching step which is subsequently added so that yellowish decelourized products are obtained. U. Meinwalt and H. O. Klingele (J. Amer. Chem. Soc. 1966, page 2071–3) have reported that a variety of oxidation products and reduction products are formed, as for example, camphoric anhydride, endo-3-hydroxycamphor, endo-3-hydroxy-epicamphor or camphonolactone, upon exposure to light of solutions of the camphor quinones in different solvents under presence of oxygen.

On the basis of these experiments, it could, however, by no means be expected, that the further exposure to light would lead to completely colourless products in the plastic matrix.

The strength properties of the plastic materials are not diminished thereby since only the initiator compounds are degraded during the post-exposure to light. Since the bleaching of these certain bicyclodiketones occurs also in the presence of light stable pigments, it is possible to produce coloured appliances as desired by application of the method according to the invention wherein the appliances do not change their shade, even over years. For opaque white pigmentation of prosthetic appliances in the anterior area, calcium fluoride has been proven, not only as filler but also as especially suitable white pigment because of its special permeability for light, which is suitable for the hardening of the photopolymerizable masses, by means of which light, even after the hardening has occured, the bleaching of the existing yellow shading can be performed without any difficulty in the bicyclodiketones used according to the invention.

Also for the method according to the invention for the production of prosthetic dental appliances of stable colour, expecially the esters of the acrylic acid and methacrylic acid have been proven useful as ethylenically unsaturated polymerizable monomers in the photopolymerizable masses. Preferably, the (meth-) acrylic ester of di-functional or poly-functional alcohols, as for example described in the DE-OS No. 28 16 823 or DE-PS No. 19 21 869, are used exclusively or in a mixture with other polyfunctional or monofunctional (meth-)acrylates. Herewith, the known organic or inorganic fillers or their mixtures can be used in addition to the conventional stabilizers, dyes and fluorescent substances. As organic fillers, prepigmented beads of polymethacrylate are preferably suitable while as inorganic fillers, quartz glasses or silicate glasses in finely ground form or mineral fillers such as e.g. calcium fluoride, are useful. Especially good results are achieved by the exclusive use or participation of micro-fine fillers, like e.g. pyrogenic silicic acid. The mentioned constituents are used in conventional quantities also in the method according to the invention.

The used fillers can be silanised, in a known manner, to improve the binding with the polymer. As silane, for instance trimethoxy-(3-methacryloxypropyl)-silane is used.

To avoid a premature polymerization, inhibitors such as e.g. p-methoxyphenol can be further added to the masses in conventional concentrations.

The colour stability with respect to the influence of sunlight of the polymerizates can be improved by the addition of known UV-stabilizers. These stabilizers should not absorb any more in considerable quantities above a wave-length of approximately 350 nm in order not to impair the photohardening step; suitable are 2-hydroxy-4-methoxybenzophenone or ethyl-2-cyano-3,3-diphenylacrylate.

The bicyclo-[2.2.1]-heptane-dione-2,3-initiators used according to the invention are added to the dental materials in quantities of 0.01 percent by weight to 1 percent by weight, preferably in a concentration of 0.05 percent by weight to 0.5 percent by weight, especially 0.1 to 0.3%. Examples for such bicyclo-[2.2.1]-heptane-diode-2,3-compounds are the norcamphor quinone (bicyclo-[2.2.1]-heptane-dione-2,3), the camphor quinone (1,7,7-trimethyl-bicyclo-[2.2.1]-heptane-dione-2,3) and the tricyclo-[5.2.1.0$^{2,6}$]-decane-dione-8,9.

As especially suitable initiator among these bicycloheptadione-compounds, the camphor quinone has been proven useful in the method according to the invention which camphor quinone preferably together with the activating amine compounds causes a rapid polymerization during the exposure of the monomers in the dental masses, and then can be bleached relatively fast through further exposure after the polymerization. As amine component, tertiary amines are especially suitable which carry preferable substituted hydrocarbon residues. Especially preferred are tertiary amines, having three hydroxy-substituted hydrocarbon groups such as triethanolamine or its derivatives. The amines are added to the mass in concentrations of 0.1 percent by weight to 10 percent by weight, preferably 0.5 percent by weight to 5 percent by weight.

During the preparation of the monomer mass, the diketone and possibly the amine are solved in the monomer and blended in simple manner with the further components, e.g. by stirring or kneading, and processed to a brushable mass. In this connection it must be kept in mind that an admission of light to the photosensitive dental mass is prevented during the production and during the storage period. Through stirring under evacuation or treatment with a roller frame or the like measures, a homogeneous, bubble-free material is produced and filled in opaque containers.

The production of the prosthetic dental appliances is preferably similar to the method according to DE-AS No. 15 16 456 in which the semi-fluid or plastic monomer mass is applied in layers on a base, each layer being thermoset before applying the next layer. In the method according to the invention, the layer of the monomer mass of requested colouring is applied with a suitable instrument, e.g. a brush or a spatula on the bridge frame or on an artificial tooth part.

Afterwards, it is exposed to an intensive light source, whereupon a new layer is applied and exposed. Through applying of the required layers, a dental appliance can be modelled, meeting the high cosmetic requirements. With a powerful light source emitting visible light (e.g. 75 Watt-halogene projector lamp), the light exposure time for each layer is between one second and twenty seconds, in most cases, approximately five seconds are sufficient. The finally modelled appliance is subjected, if necessary under cooling, to further radiation, preferably to light of a lamp emitting a high power in the wave-range between 400 and 500 nm. The light exposure is continued until the yellow shade of the bicycloheptadione compound has completely disappeared. The required exposure time is between few minutes and some hours, according to the intensity of radiation. In order to foreclose a damaging of the surface of the polymerizates by the inhibitory influence of the atmospheric oxygen, the post-exposure can occur also under vacuum; the postexposure is preferably performed at a pressure of <10 mbar. The like built up polymerized products show a very high colour stability. In this manner, jacket crowns, bridge veneers, plastic bridges, plastic inlays, orthodontical preparations and provisional crowns and bridges can be produced.

The bleaching ability through the additional treatment is a special feature of the bicyclo-[2.2.1]-heptanedione-2,3-compounds used in the method according to the invention, which compounds are from among the 1,2-diketone-initiators for the photopolymerization. This is clearly disclosed from the results of the subsequently described series of tests.

Through mixing of 35 weight percent hexandiodiacrylate, 35 weight percent bis-hydroxymethyl-tri-cyclo-[5.2.1.0$^{2,6}$]-decane-diacrylate and 30 weight percent silanised, pyrogenic silicic acid as well as 0.2 weight percent of different 1,2-diketone-photoinitiators and 1.5 weight percent triethanolamine, deformable plastic preparations were produced. Through filling in a suitable plastic mold and exposure to the visible light fraction of a 75 watt halogene projector lamp for 40 seconds, cylindrical samples having a diameter of 15 mm and a thickness of 2 mm were produced. Afterwards, the samples were subjected under air-cooling to the light of a lamp for one hour which emits high power in the wave-length range between 400 and 500 nm.

The impression of the colour has been valued visually and is shown in the following table:

| Used 1,2 diketone | Final colour of the sample | Remark |
|---|---|---|
| (a) camphor quinone | completely colourless | according to the invention |
| (b) phenanthrenequinone | canary yellow | — |
| (c) benzil | intense yellow | — |
| (d) α-naphtil | intense red | — |
| (e) p,p'-dichlorbenzil | yellow | — |
| (f) acenaphthene quinone | intense red | — |
| (g) p,p'-dimethoxybenzil | yellow | — |
| (h) diacetyl | light yellow | volatile, very unpleasant odor |
| (i) 3,4-hexandione | light yellow | very unpleasant odor |
| (j) 1,2-cyclohexandione | — | no polymerization |
| (k) furil | intense yellow | — |
| (l) 2-naphtil | intense yellow | — |
| (m) p-nitrobenzil | — | no polymerization |
| (n) 4,4,-dimethylbenzil | yellow | — |

It is obvious that from the plurality of the 1,2-diketones mentioned in the DE-OS No. 22 51 048 only the camphor quinone is useful for the formulation of a photohardenable mass, which can yield colourless prosthetic dental appliances. The more or less intensive inherent yellow colour, common to all of the 1,2-diketones, can be completely bleached out by intensive exposure to light of the polymerized mass only in the case of the camphor quinone. The other 1,2-diketones do not show this "bleaching effect"; they have shown discolourations ranging from light yellowish to intense red. Some representatives of the 1,2-diketones are additionally considered as insufficient, due to their high volatility and their very unpleasant characteristic odor.

The use of the photoinitiator systems of the certain bicycloheptanedione compounds and preferably an amine makes it possible to place one-component systems at disposal of the dental technicians, which are stable during dark storage and have further advantages besides the stability of colour. During the conventional method of hot polymerization, upon applying of the plastic mass onto a metal base (e.g. of gold or platinum alloy), tensions and gaps are obtained at the junction through the heating during the polymerization and the subsequent cooling due to the differential thermal expansion coefficient of metal and plastic, which tensions and gaps deminish the strength of the appliances. Since the photopolymerization proceeds with a comparably lower raise of temperature, these phenomena do hardly occur.

Moreover, misdosages, inhomogeneous mixtures as well as inclusions of air and the like mixing deficiencies are prevented. Furthermore, no quantities of residue must be descarded so that the material according to the invention is very economical in its utilisation.

EXAMPLE 1

A solution is prepared of 20 g hexanedioldiacrylate
20 g bis-hydroxymethyl-tricyclo[5.2.1.0$^{2,6}$]decane-diacrylate and
60 mg 1,7,7-trimethyl-bicyclo[2.2.1]-heptandione-2,3 (camphor quinone)

A powder mixture is produced of 14 g silanised, pyrogenic silicic acid dyed to tooth-like colour and
4 g calcium fluoride.

The liquid is introduced into a laboratory kneader and the powder mixture is slowly added. After a kneading-time of approximately one hour, the obtained mass is further homogenised on a roller frame and afterwards repeatedly kneaded under vacuum until a bubble-free, brushable product is obtained, showing a certain thixotropy.

When the mass is dyed in a light colour, as required for the incisal part of appliances (corresponding to the colour S11 of "Biodent" shade guide of the De Trey Company) the mass is cured in a thickness of layer of 8 mm after irradiation for 20 seconds by the light of a commercial visible light emitting lamp for dental use (Elipar-unit, ESPE Company).

The compressive strength of the polymerizate is measured at test samples of 2×2×4 mm, produced in suitable molds by primary exposure (20 seconds) with the above-mentioned irradiation unit. The specimen, at first clearly yellow-coloured, are exposed to the light of a light source for 60 minutes, irradiating with high intensity in the wavelength range between 400 and 500 nm. The specimen now obtained, which have the pure shade of the chosen shade have a compressive strength of 410 MPa after storage for 24 hours under water at 36° C.

EXAMPLE 2

Analogous to Example 1, a crown and bridge material is produced, containing as photoinitiator, instead of camphor quinone, tricyclo[5.2.1.0$^{2,6}$]-decane-dione-8,9 produced in known manner through oxidation of the tricyclo-[5.2.1.0$^{2,6}$]-decane-8-one with selenium dioxide, and dyed in light incisal colour (corresponding to colour S11 of the "Biodent" shade guide of De Trey Company). The resulting material is cured in a thickness of layer of 7 mm by an exposure as described in Example 1 (Elipar-lamp ESPE Company). In a suitable plastic mold, a cylindrical test sample is produced, having a diameter of 15 mm and a thickness of 1.5 mm through a primary exposure for 40 seconds.

After a secondary exposure time of one hour to the light of a lamp, emitting a high intensity within the range between 400 and 500 nm, the test sample, yellow coloured at first, has the pure shade of the chosen dyeing.

EXAMPLE 3

Analogous to Example 1, a crown and bridge material is produced, containing as photoinitiator instead of camphor quinone, bicyclo-[2.2.1]-heptane-diode-2,3 (norcamphor quinone) and dyed in light incisal colour (corresponding to colour S11 of the "Biodent" shade guide of the De Trey Company).

A test sample produced as in Example 2 is yellow-coloured at first and shows the pure shade of the chosen dyeing after the respective exposure (one hour).

EXAMPLE 4

In the same manner as in Example 1, a crown and bridge material is produced in whose preparation of the solution, 360 mg triethanolamine-tris-phenylurethane are added as activator. The mass is dyed in a dark brown which is required for the production of the tooth necks in dental appliances (corresponding to the colour H32 of the "Biodent" shade guide of the De Trey Company).

After light exposure for 20 seconds, the material is cured in a thickness of layer of 4 mm. Its compressive strength is 430 MPa (measured as in Example 1).

EXAMPLE 5

Production of a Jacket Crown

Analogous to Example 4, materials are produced in the requested dyeings for tooth neck, dentine and the incisive part of the tooth.

On an isolated artificial tooth part, layers are applied by a brush or a spatula in the colour and thickness required for the matching to the appearance of the natural tooth.

After applying of each layer, it is exposed to the light of a commercial dental lamp of high power within the wave-length range of 400 to 500 nm (Elipar unit ESPE Company) and the mass is subjected to the polymerization. Through secondary exposure for one hour in a vacuum of 5 mbar under air cooling to the light of a lamp which has a high power in the wave-length range between 400 and 500 nm, the yellow colour of the camphor quinone is bleached out. In order to avoid any blind spots, the position of the crown must be modified, if necessary, in such a manner, that the entire surface of the crown is sufficiently exposed to the irradiation. In that way, an abrasion-resistant crown is obtained which matches the natural tooth and has high colour stability.

EXAMPLE 6

Veneering of a bridge of precious metal

The materials produced according to Example 4 are prepared in the desired colourings.

On the bridge frame provided with conventional retentions and coated with opaque layers, the required colours are applied by layers. Each layer, as described in Example 5 is polymerized by light exposure. Even the material located behind the metal retentions is cured.

Afterwards, it is bleached out by post exposure, analogous to Example 5, if necessary, by changing the position of the bridge to expose all parts to the light.

The veneers, so obtained, excel in their colour stability and abrasion resistance. Moreover, the appearance is cosmetically completely unobjectionable.

We claim:

1. Method for production of prosthetic dental appliances by photopolymerizing of a deformable mass, comprising ethylenically unsaturated polymerizable monomer compounds and as photoinitiators, 1,2-diketones, as well as possibly fillers, dyes and inhibitors, characterized in that the mass containing a bicyclo-[2.2.1]-heptane-dione-2,3 compound as 1,2-diketone is polymerized by irradiation and then in the obtained prosthetic dental appliance the photoinitiator is bleached out through further irradiation.

2. Method as defined in claim 1, characterized in that the mass contains 0.01 to 1 percent by weight, preferably 0.05–0.5 percent by weight bicyclo-[2.2.1]-heptanedione-2,3 compound.

3. Method as defined in claims 1 and 2, characterized in that the mass contains an amine as activator.

4. Method as defined in claim 3, characterized in that the amine is a tertiary amine, carrying preferably three substituted hydrocarbon residues at the nitrogen.

5. Method as defined in claims 1 to 4, characterized in that the deformable mass is applied on a base by layers, each layer being polymerized by irradiation and cured before applying the next layer whereupon the photoinitiator is bleached out through further irradiation after the curing of the last layer in the obtained appliance.

6. Method as defined in claims 1 to 5, characterized in that camphor quinone is used as bicyclo-[2.2.1]-heptanedione-2,3 compound.

7. Method as defined in claims 1 to 6, characterized in that the bleaching is performed by an irradiation within the wave-length range between 400 and 500 nm.

8. Method as defined in claims 1 to 7, characterized in that pyrogenic silicic acid is used as filler.

9. Method as defined in claims 1 to 8, characterized in that calcium fluoride is used as filler and/or white pigment.

* * * * *